(12) United States Patent
Zhang et al.

US007655673B2

(10) Patent No.: US 7,655,673 B2
(45) Date of Patent: Feb. 2, 2010

(54) 39-DESMETHOXYRAPAMYCIN, COMPOSITIONS AND METHODS OF USE THEREOF

(75) Inventors: Mingqiang Zhang, Cambridge (GB); Rose Mary Sheridan, Little Chesterford (GB)

(73) Assignee: Biotica Technology Limited (GB)

( * ) Notice: Subject to any disclaimer, the term of this patent is extended or adjusted under 35 U.S.C. 154(b) by 0 days.

(21) Appl. No.: 11/651,669

(22) Filed: Jan. 10, 2007

(65) Prior Publication Data
US 2007/0184075 A1 Aug. 9, 2007

Related U.S. Application Data

(62) Division of application No. 11/097,605, filed on Apr. 1, 2005, now Pat. No. 7,183,289.

(30) Foreign Application Priority Data
Mar. 11, 2005 (GB) ................................. 0504995.2

(51) Int. Cl.
*A61K 31/4745* (2006.01)
(52) U.S. Cl. ........................................ 514/291; 514/80
(58) Field of Classification Search .................. 514/291
See application file for complete search history.

(56) References Cited

U.S. PATENT DOCUMENTS

| 5,708,002 | A  | 1/1998  | Luly et al.    |
|-----------|----|---------|----------------|
| 5,712,129 | A  | 1/1998  | Ford           |
| 6,485,514 | B1 | 11/2002 | Wrenn, Jr.     |
| 2003/0176915 | A1 | 9/2003 | Wright et al.  |
| 2004/0147541 | A1 | 7/2004 | Lane et al.    |
| 2005/0032825 | A1 | 2/2005 | Metcalf et al. |

FOREIGN PATENT DOCUMENTS

| WO | WO 93/16189   | 8/1993 |
|----|---------------|--------|
| WO | WO 98/02441   | 1/1998 |
| WO | WO 2004/007709| 1/2004 |
| WO | WO 2006/095173 | * 9/2006 |

OTHER PUBLICATIONS

Burkhardt et al. Rheumatol. Int., 1997, vol. 17, pp. 85-90.*
Cecil, Textbook of Medicine, 21st Edition (2000), Goldman & Bennett (Editors), W.B. Saunders Company (Publisher), Chapter 198, pp. 1060-1074.
Dhooge C et al., "P-glycoprotein is an independent prognostic factor predicting relapse in childhood acute lymphoblastic leukaemia: results of a 60year prospective study," 1999 British J Haematol. 105: 676-683.
Brown V, et al., "Rapamycin is active against B-precursor leukemai in vitro and in vivo, an effect that is modulated by IL-7-mediated signaling," 2003 PNAS 100(25): 15113-15118.
Gajra A, "Lymphoma, B-Cell," eMedicine, Jan. 10, 2005, retrieved from the internet on Nov. 20, 2005 from http://emedicine.com/med/topic1358.htm.
Lowden, P.A.S., "New Rapamycin Derivatives by Precursor-Directed Biosynthesis," ChemBioChem, 5:535-538, (2004).
Fu, L.W., et al., "The multidrug resistance of tumour cells was reversed by tetradrine in vitro and in xenografts derived from human brest adenocarcinoma MCF-7/adr cells," European Journal of Cancer, 38:418-426, (2002).
Trepanier, D.J., et al., "Rapamycin: Distribution, Pharmacokinetics and Therapeutic Range Investigations: An Update," Clinical Biochemistry, 31:345-351, (1998).
Gallant-Haidner, H.L., et al., "Pharmacokinetics and Metabolism of Sirolimus," Therapeutic Drug Monitoring, 22:31-35, (2000).
Francois G. Roberge et al.; Treatment of Autoimmune Uveoretinitis in the Rat With Rapamycin, an Inhibitor of Lymphocyte Growth Factor Signal Transduction; Current Eye Research; vol. 2(2); pp. 197-203; 1993.
Deborah A. Young et al.; IL-4, IL-10, and IL-13, and TGF-β From an Altered Peptide Ligand-Specific TH2 Cell Clone Down-Regulate Adoptive Transfer of Experimental Autoimmune Encephalomyelitis; The Journal of Immunology; vol. 164; pp. 3563-3572; 2000.
Stephen J. Pettit et al.; Evaluation of Dendritic Cell Immunogenicity After Activation and Chemical Fixation: a Mixed Lymphocyte Reaction Model; vol. 25(2), pp. 152-161; 2002.

* cited by examiner

*Primary Examiner*—Ardin Marschel
*Assistant Examiner*—James D Anderson
(74) *Attorney, Agent, or Firm*—Michael J. Herman; Paul Carango

(57) ABSTRACT

The present invention relates to medical uses of 39-desmethoxyrapamycin.

5 Claims, 4 Drawing Sheets

39-DESMETHOXYRAPAMYCIN, COMPOSITIONS AND METHODS OF USE THEREOF

This application is a divisional application of U.S. Pat. No. 7,183,289, issued Feb. 27, 2007, which claims priority under 35 U.S.C. §119(a) to Great Britain Patent Application No. 0504995.2, filed Mar. 11, 2005. The foregoing applications are incorporated by reference herein.

BACKGROUND OF THE INVENTION

Several publications and patent documents are cited throughout the specification in order to more fully describe the state of the art to which this invention pertains. The disclosure of each of these publications and patent documents is incorporated by reference herein.

Rapamycin (sirolimus) (FIG. 1) is a lipophilic macrolide produced by *Streptomyces hygroscopicus* NRRL 5491 (Sehgal et al., 1975; Vézina et al., 1975; U.S. Pat. Nos. 3,929,992; 3,993,749) with a 1,2,3-tricarbonyl moiety linked to a pipecolic acid lactone (Paiva et al., 1991). For the purpose of this invention rapamycin is described by the numbering convention of McAlpine et al. (1991) in preference to the numbering conventions of Findlay et al. (1980) or Chemical Abstracts (11$^{th}$ Cumulative Index, 1982-1986 p60719CS).

Rapamycin has significant therapeutic value due to its wide spectrum of biological activities (Huang et al., 2003). The compound is a potent inhibitor of the mammalian target of rapamycin (mTOR), a serine-threonine kinase downstream of the phosphatidylinositol 3-kinase (PI3K)/Akt (protein kinase B) signalling pathway that mediates cell survival and proliferation. This inhibitory activity is gained after rapamycin binds to the immunophilin FK506 binding protein 12 (FKBP12) (Dumont, F. J. and Q. X. Su, 1995). In T cells rapamycin inhibits signalling from the IL-2 receptor and subsequent autoproliferation of the T cells resulting in immunosuppression. Rapamycin is marketed as an immunosuppressant for the treatment of organ transplant patients to prevent graft rejection (Huang et al, 2003). In addition to immunosuppression, rapamycin has potential therapeutic use in the treatment of a number of diseases, for example, cancer, cardiovascular diseases such as restenosis, autoimmune diseases such as multiple sclerosis, rheumatoid arthritis, fungal infection and neurodegenerative diseases such as Parkinson's disease and Huntington's diseases.

Despite its utility in a variety of disease states rapamycin has a number of major drawbacks. Firstly it is a substrate of cell membrane efflux pump P-glycoprotein (P-gp, LaPlante et al, 2002, Crowe et al, 1999) which pumps the compound out of the cell making the penetration of cell membranes by rapamycin poor. This causes poor absorption of the compound after dosing. In addition, since a major mechanism of multi-drug resistance of cancer cells is via cell membrane efflux pump, rapamycin is less effective against multi-drug resistance (MDR) cancer cells. Secondly rapamycin is extensively metabolised by cytochrome P450 enzymes (Lampen et al, 1998). Its loss at hepatic first pass is high, which contributes further to its low oral bioavailability. The role of CYP3A4 and P-gp in the low bioavailability of rapamycin has been confirmed in studies demonstrating that administration of CYP3A4 and/or P-gp inhibitors decreased the efflux of rapamycin from CYP3A4-transfected Caco-2 cells (Cummins et al, 2004) and that administration of CYP3A4 inhibitors decreased the small intestinal metabolism of rapamycin (Lampen et al, 1998). The low oral bioavailability of rapamycin causes significant inter-individual variability resulting in inconsistent therapeutic outcome and difficulty in clinical management (Kuhn et al, 2001, Crowe et al, 1999).

Therefore, there is a need for the development of novel rapamycin-like compounds that are not substrates of P-gp, that may be metabolically more stable and therefore may have improved bioavailability. When used as anticancer agents, these compounds may have better efficacy against MDR cancer cells, in particular against P-gp-expressing cancer cells.

A range of synthesised rapamycin analogues using the chemically available sites of the molecule has been reported. The description of the following compounds was adapted to the numbering system of the rapamycin molecule described in FIG. 1. Chemically available sites on the molecule for derivatisation or replacement include C40 and C28 hydroxyl groups (e.g. U.S. Pat. Nos. 5,665,772; 5,362,718), C39 and C16 methoxy groups (e.g. WO 96/41807; U.S. Pat. No. 5,728, 710), C32, C26 and C9 keto groups (e.g. U.S. Pat. Nos. 5,378,836; 5,138,051; 5,665,772). Hydrogenation at C17, C19 and/or C21, targeting the triene, resulted in retention of antifungal activity but relative loss of immunosuppression (e.g. U.S. Pat. Nos. 5,391,730; 5,023,262). Significant improvements in the stability of the molecule (e.g. formation of oximes at C32, C40 and/or C28, U.S. Pat. Nos. 5,563,145, 5,446,048), resistance to metabolic attack (e.g. U.S. Pat. No. 5,912,253), bioavailability (e.g. U.S. Pat. Nos. 5,221,670; 5,955,457; WO 98/04279) and the production of prodrugs (e.g. U.S. Pat. Nos. 6,015,815; 5,432,183) have been achieved through derivatisation.

Two of the most advanced rapamycin derivatives in clinical development are 40-O-(2-hydroxy)ethyl-rapamycin (RAD001, Certican, everolimus) a semi-synthetic analogue of rapamycin that shows immunosuppressive pharmacological effects (Sedrani, R. et al., 1998; Kirchner et al., 2000; U.S. Pat. No. 5,665,772) and 40-O[2,2-bis(hydroxymethyl)propionyoxy]rapamycin, CCI-779 (Wyeth-Ayerst) an ester of rapamycin which inhibits cell growth in vitro and inhibits tumour growth in vivo (Yu et al., 2001). CCI-779 is currently in Phase III clinical trials. Studies investigating the pharmacokinetics of RAD001 have shown that, similarly to rapamycin, it is a substrate for P-gp (Crowe et al, 1999, LaPlante et al, 2002).

The present invention provides the novel and surprising use of 39-desmethoxyrapamycin in medicine, particularly in the treatment of cancer or B-cell malignancies, in the induction or maintenance of immunosuppression, the stimulation of neuronal regeneration or the treatment of fungal infections, transplantation rejection, graft vs. host disease, autoimmune disorders, diseases of inflammation vascular disease and fibrotic diseases. In particular the present invention provides for the use of 39-desmethoxyrapamycin in the treatment of cancer and B-cell malignancies. Despite its close structural similarity to rapamycin the compound of the invention displays a surprisingly different pharmacological profile. In particular it has significantly increased cell membrane permeability and decreased efflux in comparison with rapamycin, and it is not a substrate for P-gp. Additionally, this compound shows more potent activity against multi-drug resistant and P-gp-expressing cancer cell lines than rapamycin. When compared with rapamycin it shows a significantly different inhibitory profile against the NCI 60 cell line panels. 39-Desmethoxyrapamycin also shows increased metabolic stability with respect to rapamycin.

Therefore, the present invention provides for the medical use of 39-desmethoxyrapamycin, a rapamycin analogue with improved metabolic stability, improved cell membrane permeability, a decreased rate of efflux and a different tumour cell inhibitory profile to rapamycin. This compound is useful in medicine, in particular for the treatment of cancer and/or B-cell malignancies, in the induction or maintenance of immunosuppression, the stimulation of neuronal regeneration or the treatment of fungal infections, transplantation rejection, graft vs. host disease, autoimmune disorders, diseases of inflammation vascular disease and fibrotic diseases. The present invention particularly provides for the use of 39-desmethoxyrapamycin in the treatment of cancer and/or B-cell malignancies.

SUMMARY OF THE INVENTION

The present invention relates to the medical use of 39-desmethoxyrapamycin, particularly in the treatment of cancer and/or B-cell malignancies, the induction or maintenance of immunosuppression, the treatment of transplantation rejection, graft vs. host disease, autoimmune disorders, diseases of inflammation, vascular disease and fibrotic diseases, the stimulation of neuronal regeneration or the treatment of fungal infections. In particular this invention relates to the use of 39-desmethoxyrapamycin for the treatment of cancer and B-cell malignancies.

Definitions

The articles "a" and "an" are used herein to refer to one or to more than one (i.e. at least one) of the grammatical objects of the article. By way of example "an analogue" means one analogue or more than one analogue.

As used herein, the term "autoimmune disorder(s)" includes, without limitation: systemic lupus erythrematosis (SLE), rheumatoid arthritis, myasthenia gravis and multiple sclerosis.

As used herein, the term "diseases of inflammation" includes, without limitation: psoriasis, dermatitis, eczema, seborrhoea, inflammatory bowel disease (including but not limited to ulcerative colitis and Crohn's disease), pulmonary inflammation (including asthma, chronic obstructive pulmonary disease, emphysema, acute respiratory distress syndrome and bronchitis), rheumatoid arthritis and eye uveitis.

As used herein, the term "cancer" refers to a malignant growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types, such as but not limited to, melanoma, lymphoma, leukaemia, fibrosarcoma, rhabdomyosarcoma, and mastocytoma and types of tissue carcinoma, such as but not limited to, colorectal cancer, prostate cancer, small cell lung cancer and non-small cell lung cancer, breast cancer, pancreatic cancer, bladder cancer, renal cancer, gastric cancer, gliobastoma, primary liver cancer and ovarian cancer.

As used herein the term "B-cell malignancies" includes a group of disorders that include chronic lymphocytic leukaemia (CLL), multiple myeloma, and non-Hodgkin's lymphoma (NHL). They are neoplastic diseases of the blood and blood forming organs. They cause bone marrow and immune system dysfunction, which renders the host highly susceptible to infection and bleeding.

As used herein, the term "vascular disease" includes, without limitation: hyperproliferative vascular disorders (e.g. restenosis and vascular occlusion), graft vascular atherosclerosis, cardiovascular disease, cerebral vascular disease and peripheral vascular disease (e.g. coronary artery disease, arteriosclerosis, atherosclerosis, nonatheromatous arteriosclerosis or vascular wall damage).

As used herein the terms "neuronal regeneration" refers to the stimulation of neuronal cell growth and includes neurite outgrowth and functional recovery of neuronal cells. Diseases and disorders where neuronal regeneration may be of significant therapeutic benefit include, but are not limited to, Alzheimer's disease, Parkinson's disease, Huntingdon's chorea, amyotrophic lateral sclerosis, trigeminal neuralgia, glossopharyngeal neuralgia, Bell's palsy, muscular dystrophy, stroke, progressive muscular atrophy, progressive bulbar inherited muscular atrophy, cervical spondylosis, Gullain-Barre syndrome, dementia, peripheral neuropathies and peripheral nerve damage, whether caused by physical injury (e.g. spinal cord injury or trauma, sciatic or facial nerve lesion or injury) or a disease state (e.g. diabetes).

As used herein the term "fibrotic diseases" refers to diseases associated with the excess production of the extracellular matrix and includes (without limitation) sarcoidosis, keloids, glomerulonephritis, end stage renal disease, liver fibrosis (including but not limited to cirrhosis, alcohol liver disease and steato-heptatitis), chronic graft nephropathy, surgical adhesions, vasculopathy, cardiac fibrosis, pulmonary fibrosis (including but not limited to idiopathic pulmonary fibrosis and cryptogenic fibrosing alveolitis), macular degeneration, retinal and vitreal retinopathy and chemotherapy or radiation-induced fibrosis.

As used herein, the term "graft vs. host disease" refers to a complication that is observed after allogeneic stem cell/bone marrow transplant. It occurs when infection-fighting cells from the donor recognize the patient's body as being different or foreign. These infection-fighting cells then attack tissues in the patient's body just as if they were attacking an infection. GvHD is categorized as acute when it occurs within the first 100 days after transplantation and chronic if it occurs more than 100 days after transplantation. Tissues typically involved include the liver, gastrointestinal tract and skin. Chronic graft vs. host disease occurs approximately in 10-40 percent of patients after stem cell/bone marrow transplant.

As used herein, the term "bioavailability" refers to the degree to which or rate at which a drug or other substance is absorbed or becomes available at the site of biological activity after administration. This property is dependent upon a number of factors including the solubility of the compound, rate of absorption in the gut, the extent of protein binding and metabolism etc. Various tests for bioavailability that would be familiar to a person of skill in the art are described herein (see also Trepanier et al, 1998, Gallant-Haidner et al, 2000).

As used herein, the term "39-desmethoxyrapamycin" refers to a compound according to formula (A) in FIG. 2, or a pharmaceutically acceptable salt thereof. This compound is also referred to as the "compound of the invention" and these terms are used interchangeably in the present application.

The pharmaceutically acceptable salts of 39-desmethoxyrapamycin include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lacetic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both 39-desmethoxyrapamycin and its pharmaceutically acceptable salts.

DESCRIPTION OF THE INVENTION

The present invention relates to the use of 39-desmethoxyrapamycin in medicine, in particular in the treatment of cancer, B-cell malignancies, the induction or maintenance of immunosuppression, the treatment of transplantation rejection, graft vs. host disease, autoimmune disorders, diseases of inflammation, vascular disease and fibrotic diseases, the stimulation of neuronal regeneration or the treatment of fungal infections. In particular this invention relates to the use of 39-desmethoxyrapamycin for the treatment of cancer and B-cell malignancies.

In an alternative embodiment, the present invention provides a method for the treatment of cancer or B-cell malignancies, a method of induction or maintenance of immunosuppression, the stimulation of neuronal regeneration, a method for the treatment of fungal infections, transplantation rejection, graft vs. host disease, autoimmune disorders, diseases of inflammation vascular disease or fibrotic diseases which comprises administering to a patient an effective amount of 39-desmethoxyrapamycin. Preferably, the present invention provides a method of treatment of cancer or B-cell malignancies which comprises administering to a patient an effective amount of 39-desmethoxyrapamycin.

The present invention also provides the use of 39-desmethoxyrapamycin in the manufacture of a medicament for treatment of cancer or B-cell malignancies, for induction or maintenance of immunosuppression, for stimulation of neuronal regeneration, for the treatment of fungal infections, transplantation rejection, graft vs. host disease, autoimmune disorders, diseases of inflammation vascular disease or fibrotic diseases.

39-Desmethoxyrapamycin is a close structural analogue of rapamycin that is made using the methods described in WO 04/007709. However it shows a different spectrum of activity to rapamycin as shown by the COMPARE analysis of the NCI 60 cell line panel. The COMPARE analysis uses a Pearson analysis to compare the activity of two compounds on the NCI 60-cell line panel and produces a correlation coefficient which indicates how similar the two compounds spectra of activity are and this may indicate how related their mechanism's of action are. The Pearson coefficient for rapamycin and 39-desmethoxyrapamycin is 0.614, this should be compared to the Pearson coefficient between rapamycin and CCI-779 (a 40-hydroxy ester derivative of rapamycin) which is 0.86 (Dancey, 2002). Therefore, 39-desmethoxyrapamycin has a different spectrum of activity compared to rapamycin.

Multi-Drug Resistance (MDR) is a significant problem in the treatment of cancer and B-cell malignancies. It is the principle reason behind the development of drug resistance in many cancers (Persidis A, 1999). MDR is associated with increased level of adenosine triphosphate binding cassette transporters (ABC transporters), in particular an increase in the expression of the MDR1 gene which encodes for P-glycoprotein (P-gp) or the MRP1 gene which encodes MRP1. The level of MDR1 gene expression varies widely across different cancer-derived cell lines, in some cell lines it is undetectable, whereas in others may show up to a 10 or 100-fold increased expression relative to standard controls.

Some of the indicated difference in the spectrum of activity between rapamycin and 39-desmethoxyrapamycin may be explained because 39-desmethoxyrapamycin is not a substrate for P-gp. 39-Desmethoxyrapamycin has a decreased efflux from Caco-2 cells compared to rapamycin and was shown not to be a substrate for P-gp in an in vitro P-gp substrate assay (see examples herein).

Therefore, a further aspect of the invention provides for the use of 39-desmethoxyrapamycin in the treatment of a cancer or B-cell malignancy resistant to one or more existing anti-cancer agent(s) ie MDR cancers or B-cell malignancies. In a specific aspect the present invention provides for the use of 39-desmethoxyrapamycin in the treatment of P-gp-expressing cancers or B-cell malignancies. In a yet more preferred embodiment the present invention provides for the use of 39-desmethoxyrapamycin in the treatment of high P-gp expressing cancers or B-cell malignancies. Particularly, high P-gp expressing cancers or B-cell malignancies may have 2-fold, 5-fold, 10-fold, 20-fold, 25-fold, 50-fold or 100-fold increased expression relative to control levels. Suitable controls are cells which do not express P-gp, which have a low expression level of P-gp or which have low MDR function, a person of skill in the art is aware of or can identify such cell lines; by way of example (but without limitation) suitable cell lines include: MDA435/LCC6, SBC-3/CDDP, MCF7, NCI-H23, NCI-H522, A549/ATCC, EKVX, NCI-H226, NCI-H322M, NCI-H460, HOP-18, HOP-92, LXFL 529, DMS 114, DMS 273, HT29, HCC-2998, HCT-116, COLO 205, KM12, KM20L2, MDA-MB-231/ATCC, MDA-MB-435, MDA-N, BT-549, T-47D, OVCAR-3, OVCAR-4, OVCAR-5, OVCAR-8, IGROV1, SK-OV-3, K-562, MOLT-4, HL-60 (TB), RPMI-8226, SR, SN12C, RXF-631, 786-0, TK-10, LOX IMVI, MALME-3M, SK-MEL-2, SK-MEL-5, SK-MEL-28, M14, UACC-62, UACC-257, PC-3, DU-145, SNB-19, SNB-75, SNB-78, U251, SF-268, SF-539, XF 498.

In an alternative aspect the present invention provides for the use of 39-desmethoxyrapamycin in the preparation of a medicament for use in the treatment of MDR cancers or B-cell malignancies. In a specific aspect the present invention provides for the use of 39-desmethoxyrapamycin in the preparation of a medicament for use in the treatment of P-gp-expressing cancers or B-cell malignancies. In a yet more preferred embodiment the present invention provides for the use of 39-desmethoxyrapamycin in the preparation of a medicament for use in the treatment of high P-gp expressing cancers or B-cell malignancies. Particularly, high P-gp expressing cancers or B-cell malignancies may have 2-fold, 5-fold, 10-fold, 20-fold, 25-fold, 50-fold or 100-fold increased expression relative to control levels. Suitable controls are described above.

Methods for determining the expression level of P-gp in a sample are discussed further herein.

Therefore, in a further aspect the present invention provides a method for the treatment of P-gp-expressing-cancers or B-cell malignancies comprising administering a therapeutically effective amount of 39-desmethoxyrapamycin. The expression level of P-glycoprotein (P-gp) in a particular cancer type may be determined by a person of skill in the art using techniques including but not limited to real time RT-PCR (Szakács et al, 2004; Stein et al, 2002; Langmann et al; 2003), by immunohistochemistry (Stein et al, 2002) or using microarrays (Lee et al, 2003), these methods are provided as examples only, other suitable methods will occur to a person of skill in the art.

39-Desmethoxyrapamycin shows increased metabolic stability compared to rapamycin as shown herein in the examples. A number of papers have previously identified the 39-methoxy group on rapamycin as being a major site of metabolic attack to convert rapamycin to 39-O-desmethylrapamycin (Trepanier et al, 1998). The major metabolites of rapamycin have significantly decreased activity when compared to the parent compound (Gallant-Haidner et al, 2000, Trepanier et al, 1998). In contrast, 39-desmethoxyrapamycin no longer has available the most significant sites of metabolic attack, which results in an increased stability of the compounds (see examples). Coupled with the higher or equivalent potency of 39-desmethoxyrapamycin to the rapamycin parent compound this provides a longer half-life for the compound of the invention. This is a further surprising advantage of 39-desmethoxyrapamycin over rapamycin.

The properties of 39-desmethoxyrapamycin described above (that it is not a substrate for P-gp, has increased metabolic stability and decreased efflux from cells via P-gp) indicate that 39-desmethoxyrapamycin has improved bioavailability compared to its parent compound rapamycin. Therefore, the present invention provides for the use of 39-desmethoxyrapamycin, a rapamycin analogue with improved metabolic stability, improved cell membrane permeability and a distinct cancer cell inhibitory profile, in medicine, particularly in the treatment of cancer or B-cell malignancies.

A further surprising feature of this invention is the potency of the compound. Experiments have shown that desmethyl metabolites of rapamycin, in particular 39-O-desmethylrapamycin, show a large decrease in activity compared to the parent rapamycin compound, 10% of the mixed lymphocyte reaction (MLR)/immunosuppressive activity and 15-34% of the in vitro FKBP binding (Gallant-Haidner et al, 2000, Trepanier et al, 1998). Therefore, a person of skill in the art would logically expect that the 39-desmethoxy analogue of rapamycin would have similarly low activity. Thus based on the information present in the public domain as of the priority date of the present application, a person of skill in the art would not have thought to pursue 39-desmethoxyrapamycin with a reasonable expectation of success. However, surprisingly, 39-desmethoxyrapamycin has equivalent or improved potency when compared to rapamycin in a number of assays (as shown in the examples herein).

The present invention also provides a pharmaceutical composition comprising 39-desmethoxyrapamycin, or a pharmaceutically acceptable salt thereof, together with a pharmaceutically acceptable carrier.

Rapamycin and related compounds that are or have been in clinical trials, such as CCI-779 and RAD001 have poor pharmacological profiles, including poor metabolic stability, poor permeability, high levels of efflux via P-gp and poor bioavailability. The present invention provides for the use of 39-desmethoxyrapamycin or a pharmaceutically acceptable salt thereof which has improved pharmaceutical properties compared to rapamycin.

A person of skill in the art will be able to determine the pharmacokinetics and bioavailability of a compound of the invention using in vivo and in vitro methods known to a person of skill in the art, including but not limited to those described below and in Gallant-Haidner et al, 2000 and Trepanier et al, 1998 and references therein. The bioavailability of a compound is determined by a number of factors, (e.g. water solubility, cell membrane permeability, the extent of protein binding and metabolism and stability) each of which may be determined by in vitro tests as described in the examples herein, it will be appreciated by a person of skill in the art that an improvement in one or more of these factors will lead to an improvement in the bioavailability of a compound. Alternatively, the bioavailability of 39-desmethoxyrapamycin or a pharmaceutically acceptable salt thereof may be measured using in vivo methods as described in more detail below.

In Vivo Assays

In vivo assays may also be used to measure the bioavailability of a compound such as 39-desmethoxyrapamcyin. Generally, said compound is administered to a test animal (e.g. mouse or rat) both intraperitoneally (i.p.) or intravenously (i.v.) and orally (p.o.) and blood samples are taken at regular intervals to examine how the plasma concentration of the drug varies over time. The time course of plasma concentration over time can be used to calculate the absolute bioavailability of the compound as a percentage using standard models. An example of a typical protocol is described below.

Mice are dosed with 3 mg/kg of 39-desmethoxyrapamycin i.v. or 10 mg/kg of 39-desmethoxyrapamycin p.o. Blood samples are taken at 5 min, 15 min, 1 h, 4 h and 24 h intervals, and the concentration of 39-desmethoxyrapamycin in the sample is determined via HPLC. The time-course of plasma concentrations can then be used to derive key parameters such as the area under the plasma concentration-time curve (AUC—which is directly proportional to the total amount of unchanged drug that reaches the systemic circulation), the maximum (peak) plasma drug concentration, the time at which maximum plasma drug concentration occurs (peak time), additional factors which are used in the accurate determination of bioavailability include: the compound's terminal half life, total body clearance, steady-state volume of distribution and F %. These parameters are then analysed by non-compartmental or compartmental methods to give a calculated percentage bioavailability, for an example of this type of method see Gallant-Haidner et al, 2000 and Trepanier et al, 1998, and references therein.

The aforementioned compound of the invention or a formulation thereof may be administered by any conventional method for example but without limitation they may be administered parenterally, orally, topically (including buccal, sublingual or transdermal), via a medical device (e.g. a stent), by inhalation or via injection (subcutaneous or intramuscular). The treatment may consist of a single dose or a plurality of doses over a period of time.

Whilst it is possible for 39-desmethoxyrapamycin to be administered alone, it is preferable to present it as a pharmaceutical formulation, together with one or more acceptable carriers. The carrier(s) must be "acceptable" in the sense of being compatible with the compound of the invention and not deleterious to the recipients thereof. Examples of suitable carriers are described in more detail below.

39-Desmethoxyrapamycin may be administered alone or in combination with other therapeutic agents, co-administration of two (or more) agents allows for significantly lower doses of each to be used, thereby reducing the side effects seen. The increased metabolic stability of 39-desmethoxyrapamyin has an extra advantage over rapamycin in that it is less likely to cause drug-drug interactions when used in combination with drugs that are substrates of P450 enzymes as occurs with rapamycin (Lampen et al, 1998).

Therefore in one embodiment, 39-desmethoxyrapamycin is co-administered with another therapeutic agent for the induction or maintenance of immunosuppression, for the treatment of transplantation rejection, graft vs. host disease, autoimmune disorders or diseases of inflammation preferred agents include, but are not limited to, immunoregulatory agents e.g. azathioprine, corticosteroids, cyclophosphamide, cyclosporin A, FK506, Mycophenolate Mofetil, OKT-3 and ATG.

In a alternative embodiment, 39-desmethoxyrapamycin is co-administered with another therapeutic agent for the treatment of cancer or B-cell malignancies preferred agents include, but are not limited to, methotrexate, leukovorin, adriamycin, prenisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin™), capecitabine, raloxifene hydrochloride, EGFR inhibitors (e.g. Iressa®, Tarceva™, Erbitux™), VEGF inhibitors (e.g. Avastin™), proteasome inhibitors (e.g. Velcade™), Glivec® or hsp90 inhibitors (e.g. 17-AAG). Additionally, 39-desmethoxyrapamyin may be administered in combination with other therapies including, but not limited to, radiotherapy or surgery.

In one embodiment, 39-desmethoxyrapamycin is co-administered with another therapeutic agent for the treatment of vascular disease, preferred agents include, but are not limited to, ACE inhibitors, angiotensin II receptor antagonists, fibric acid derivatives, HMG-CoA reductase inhibitors, beta adrenergic blocking agents, calcium channel blockers, antioxidants, anticoagulants and platelet inhibitors (e.g. Plavix™).

In one embodiment, 39-desmethoxyrapamycin is co-administered with another therapeutic agent for the stimulation of neuronal regeneration, preferred agents include, but are not limited to, neurotrophic factors e.g. nerve growth factor, glial derived growth factor, brain derived growth factor, ciliary neurotrophic factor and neurotrophin-3.

In one embodiment, 39-desmethoxyrapamycin is co-administered with another therapeutic agent for the treatment of fungal infections; preferred agents include, but are not limited to, amphotericin B, flucytosine, echinocandins (e.g. caspofungin, anidulafungin or micafungin), griseofulvin, an imidazole or a triazole antifungal agent (e.g. clotrimazole, miconazole, ketoconazole, econazole, butoconazole, oxiconazole, terconazole, itraconazole, fluconazole or voriconazole).

By co-administration is included any means of delivering two or more therapeutic agents to the patient as part of the same treatment regime, as will be apparent to the skilled person. Whilst the two or more agents may be administered simultaneously in a single formulation this is not essential. The agents may administered in different formulations and at different times.

The formulations may conveniently be presented in unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

39-Desmethoxyrapamycin will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

For example, 39-desmethoxyrapamycin can be administered orally, buccally or sublingually in the form of tablets, capsules, ovules, elixirs, solutions or suspensions, which may contain flavouring or colouring agents, for immediate-, delayed- or controlled-release applications.

Solutions or suspensions of 39-desmethoxyrapamycin suitable for oral administration may also contain excipients e.g. N,N-dimethylacetamide, dispersants e.g. polysorbate 80, surfactants, and solubilisers, e.g. polyethylene glycol, Phosal 50 PG (which consists of phosphatidylcholine, soya-fatty acids, ethanol, mono/diglycerides, propylene glycol and ascorbyl palmitate), Such tablets may contain excipients such as microcrystalline cellulose, lactose (e.g. lactose monohydrate or lactose anyhydrous), sodium citrate, calcium carbonate, dibasic calcium phosphate and glycine, butylated hydroxytoluene (E321), crospovidone, hypromellose, disintegrants such as starch (preferably corn, potato or tapioca starch), sodium starch glycollate, croscarmellose sodium, and certain complex silicates, and granulation binders such as polyvinylpyrrolidone, hydroxypropylmethylcellulose (HPMC), hydroxypropylcellulose (HPC), macrogol 8000, sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

It should be understood that in addition to the ingredients particularly mentioned above the formulations of this invention may include other agents conventional in the art having regard to the type of formulation in question, for example those suitable for oral administration may include flavouring agents.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollient in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base.

Alternatively, the active agent may be formulated in a cream with an oil-in-water cream base or a water-in-oil base.

For parenteral administration, fluid unit dosage forms are prepared utilizing the active ingredient and a sterile vehicle, for example but without limitation water, alcohols, polyols, glycerine and vegetable oils, water being preferred. The active ingredient, depending on the vehicle and concentration used, can be either suspended or dissolved in the vehicle. In preparing solutions the active ingredient can be dissolved in water for injection and filter sterilised before filling into a suitable vial or ampoule and sealing.

Advantageously, agents such as local anaesthetics, preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

Parenteral suspensions are prepared in substantially the same manner as solutions, except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

39-Desmethoxyrapamyin may also be administered using medical devices known in the art. For example, in one embodiment, a pharmaceutical composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. In a specific embodiment 39-desmethoxyrapamycin? may be administered using a drug-eluting stent, for example one corresponding to those described in WO 01/87263 and related publications or those described by Perin (Perin, EC, 2005). Many other such implants, delivery systems, and modules are known to those skilled in the art.

The dosage to be administered of a compound of the invention will vary according to the particular compound, the disease involved, the subject, and the nature and severity of the disease and the physical condition of the subject, and the selected route of administration. The appropriate dosage can be readily determined by a person skilled in the art.

The compositions may contain from 0.1% by weight, preferably from 5-60%, more preferably from 10-30% by weight, of a compound of invention, depending on the method of administration.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

EXAMPLES

Materials & Methods

Materials

Figure 1:
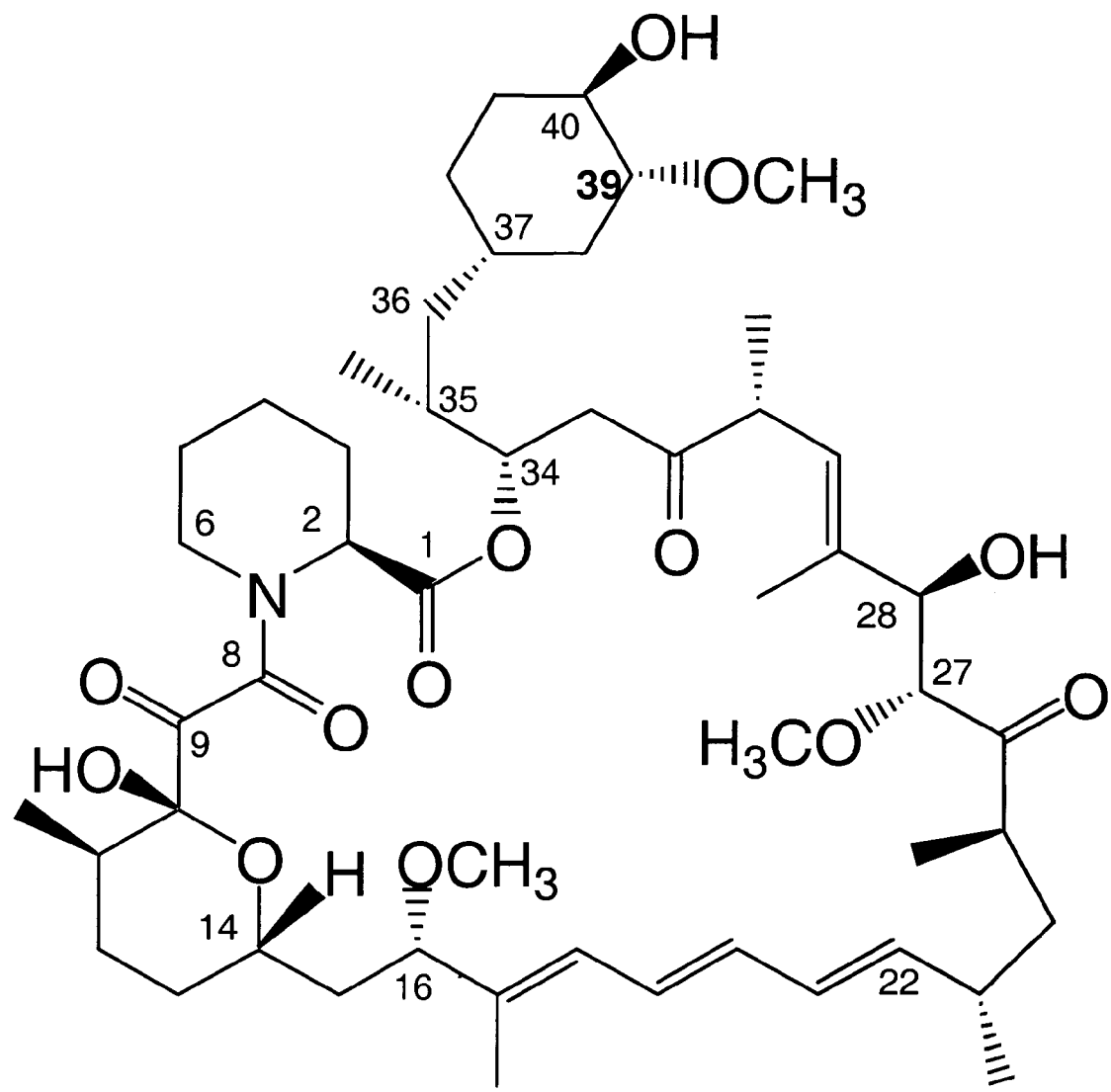
FIG. 1: shows the structure of rapamycin

Unless otherwise indicated, all reagents used in the examples below were obtained from commercial sources.

Culture

*S. hygroscopicus* MG2-10 [IJMNOQLhis] (WO 04/007709; Gregory et al., 2004) was maintained on medium 1 agar plates (see below) at 28° C. Spore stocks were prepared after growth on medium 1, preserved in 20% w/v glycerol: 10% w/v lactose in distilled water and stored at −80° C. Vegetative cultures were prepared by inoculating 0.1 mL of frozen stock into 50 mL medium 2 (see below) in 250 mL flask. The culture was incubated for 36 to 48 hours at 28° C., 300 rpm.

Production Method:

Vegetative cultures were inoculated at 2.5-5% v/v into medium 3. Cultivation was carried out for 6-7 days, 26° C., 300 rpm.

Feeding Procedure:

The feeding/addition of cyclohexane carboxylic acid was carried out 24-48 hours after inoculation and was fed at 1-2 mM final concentration unless stated otherwise.

Medium 1:

| component | Source | Catalogue # | Per L |
|---|---|---|---|
| Corn steep powder | Sigma | C-8160 | 2.5 g |
| Yeast extract | Difco | 0127-17 | 3 g |
| Calcium carbonate | Sigma | C5929 | 3 g |
| Iron sulphate | Sigma | F8633 | 0.3 g |
| BACTO agar | | | 20 g |
| Wheat starch | Sigma | S2760 | 10 g |
| Water to | | | 1 L |

The media was then sterilised by autoclaving 121° C., 20 min.

Medium 2: Rap V7 Seed Medium

| Component | Per L |
|---|---|
| Toasted Nutrisoy (ADM Ingredients Ltd) | 5 g |
| Avedex W80 dextrin (Deymer Ingredients Ltd) | 35 g |
| Corn Steep Solids (Sigma) | 4 g |
| Glucose | 10 g |
| $(NH_4)_2SO_4$ | 2 g |
| Lactic acid (80%) | 1.6 mL |
| $CaCO_3$ (Caltec) | 7 g |

Adjust pH to 7.5 with 1 M NaOH.

The media was then sterilised by autoclaving 121° C., 20 min.

After sterilisation 0.16 mL of 40% glucose is added to each 7 mL of media.

Medium 3: MD6 Medium (Fermentation Medium)

| Component | Per L |
|---|---|
| Toasted Nutrisoy (ADM Ingredients Ltd) | 30 g |
| Corn starch (Sigma) | 30 g |
| Avedex W80 dextrin (Deymer Ingredients Ltd) | 19 g |
| Yeast (Allinson) | 3 g |
| Corn Steep Solids (Sigma) | 1 g |
| $KH_2PO_4$ | 2.5 g |
| $K_2HPO_4$ | 2.5 g |
| $(NH_4)_2SO_4$ | 10 g |
| NaCl | 5 g |
| $CaCO_3$ (Caltec) | 10 g |
| $MnCl_2 \cdot 4H_2O$ | 10 mg |
| $MgSO_4 \cdot 7H_2O$ | 2.5 mg |
| $FeSO_4 \cdot 7H_2O$ | 120 mg |
| $ZnSO_4 \cdot 7H_2O$ | 50 mg |
| MES (2-morpholinoethane sulphuric acid monohydrate) | 21.2 g | pH is corrected to 6.0 with 1 M NaOH

Before sterilization 0.4 mL of Sigma α-amylase (BAN 250) was added to 1 L of medium.

Medium was sterilised for 20 min at 121° C.

After sterilisation 0.35 mL of sterile 40% fructose and 0.10 mL of L-lysine (140 mg/mL in water, filter-sterilsed) was added to each 7 mL.

Medium 4: Rap V7a Seed Medium

| Component | Per L |
|---|---|
| Toasted Nutrisoy (ADM Ingredients Ltd) | 5 g |
| Avedex W80 dextrin (Deymer Ingredients Ltd) | 35 g |
| Corn Steep Solids (Sigma) | 4 g |
| $(NH_4)_2SO_4$ | 2 g |
| Lactic acid (80%) | 1.6 mL |
| $CaCO_3$ (Caltec) | 7 g |

Adjust pH to 7.5 with 1 M NaOH.

The media was then sterilised by autoclaving 121° C., 20 min.

Medium 5: MD6/5-1 Medium (Fermentation Medium)

| Component | Per L |
|---|---|
| Toasted Nutrisoy (ADM Ingredients Ltd) | 15 g |
| Avedex W80 dextrin (Deymer Ingredients Ltd) | 50 g |
| Yeast (Allinson) | 3 g |
| Corn Steep Solids (Sigma) | 1 g |
| $KH_2PO_4$ | 2.5 g |
| $K_2HPO_4$ | 2.5 g |
| $(NH_4)_2SO_4$ | 10 g |
| NaCl | 13 g |
| $CaCO_3$ (Caltec) | 10 g |
| $MnCl_2 \cdot 4H_2O$ | 3.5 mg |
| $MgSO_4 \cdot 7H_2O$ | 15 mg |
| $FeSO_4 \cdot 7H_2O$ | 150 mg |
| $ZnSO_4 \cdot 7H_2O$ | 60 mg |
| SAG 471 | 0.1 ml |

Medium was sterilised for 30 min at 121° C.

After sterilisation 15 g of Fructose per L was added.

After 48 h 0.5 g/L of L-lysine was added.

Analytical Methods

Method A

Injection volume: 0.005-0.1 mL (as required depending on sensitivity). HPLC was performed on Agilent "Spherisorb" "Rapid Resolution" cartridges SB C8, 3 micron, 30 mm×2.1 mm, running a mobile phase of:

Mobile phase A: 0.01% Formic acid in pure water
Mobile phase B: 0.01% Formic acid in Acetonitrile
Flow rate: 1 mL/minute.

Linear gradient was used, from 5% B at 0 min to 95% B at 2.5 min holding at 95% B until 4 min returning to 5% B until next cycle. Detection was by UV absorbance at 254 nm and/or by mass spectrometry electrospray ionisation (positive or negative) using a Micromasss Quattro-Micro instrument.

Method B

Injection volume: 0.02 mL. HPLC was performed on 3 micron BDS C18 Hypersil (ThermoHypersil-Keystone Ltd) column, 150×4.6 mm, maintained at 50° C., running a mobile phase of:

Mobile phase A: Acetonitrile (100 mL), trifluoracetic acid (1 mL), 1 M ammonium acetate (10 mL) made up to 1 L with deionised water.
Mobile phase B: Deionised water (100 mL), trifluoracetic acid (1 mL), 1M ammonium acetate (10 mL) made up to 1 L with acetonitrile.
Flow rate: 1 mL/minute.

A linear gradient from 55% B-95% B was used over 10 minutes, followed by 2 minutes at 95% B, 0.5 minutes to 55%

B and a further 2.5 minutes at 55% B. Compound detection was by UV absorbance at 280 nm.

Method C

The HPLC system comprised an Agilent HP1100 and was performed on 3 micron BDS C18 Hypersil (ThermoHypersil-Keystone Ltd) column, 150×4.6 mm, maintained at 40° C., running a mobile phase of:

Mobile phase A: deionised water.
Mobile phase B: acetonitrile.
Flow rate: 1 mL/minute.

This system was coupled to a Bruker Daltonics Esquire3000 electrospray mass spectrometer. Positive negative switching was used over a scan range of 500 to 1000 Dalton.

A linear gradient from 55% B-95% B was used over 10 minutes, followed by 2 minutes at 95% B, 0.5 minutes to 55% B and a further 2.5 minutes at 55% B.

In Vitro Bioassay for Anticancer Activity

In vitro evaluation of compounds for anticancer activity in a panel of 12 human tumour cell lines in a monolayer proliferation assay were carried out at the Oncotest Testing Facility, Institute for Experimental Oncology, Oncotest GmbH, Freiburg. The characteristics of the 12 selected cell lines is summarised in Table 1.

TABLE 1

Test cell lines

| # | Cell line | Characteristics |
|---|---|---|
| 1 | MCF-7 | Breast, NCI standard |
| 2 | MDA-MB-231 | Breast - PTEN positive, resistant to 17-AAG |
| 3 | MDA-MB-468 | Breast - PTEN negative, resistant to 17-AAG |
| 4 | NCI-H460 | Lung, NCI standard |
| 5 | SF-268 | CNS, NCI standard |
| 6 | OVCAR-3 | Ovarian - p85 mutated. AKT amplified. |
| 7 | A498 | Renal, high MDR expression, |
| 8 | GXF 251L | Gastric |
| 9 | MEXF 394NL | Melanoma |
| 10 | UXF 1138L | Uterus |
| 11 | LNCAP | Prostate - PTEN negative |
| 12 | DU145 | Prostate - PTEN positive |

The Oncotest cell lines were established from human tumor xenografts as described by Roth et al. 1999. The origin of the donor xenografts was described by Fiebig et al. 1992. Other cell lines were either obtained from the NCI (H460, SF-268, OVCAR-3, DU145, MDA-MB-231, MDA-MB-468) or purchased from DSMZ, Braunschweig, Germany (LNCAP).

All cell lines, unless otherwise specified, are grown at 37° C. in a humidified atmosphere (95% air, 5% $CO_2$) in a 'ready-mix' medium containing RPMI 1640 medium, 10% fetal calf serum, and 0.1 mg/mL gentamicin (PAA, Cölbe, Germany).

Monolayer Assay—Protocol 1:

A modified propidium iodide assay was used to assess the effects of the test compound(s) on the growth of twelve human tumor cell lines (Dengler et al, 1995).

Briefly, cells were harvested from exponential phase cultures by trypsinization, counted and plated in 96 well flat-bottomed microtitre plates at a cell density dependent on the cell line (5-10.000 viable cells/well). After 24 h recovery to allow the cells to resume exponential growth, 0.01 mL of culture medium (6 control wells per plate) or culture medium containing 39-desmethoxyrapamycin were added to the wells. Each concentration was plated in triplicate. 39-Desmethoxyrapamycin was applied in two concentrations (0.001 mM and 0.01 mM). Following 4 days of continuous incubation, cell culture medium with or without 39-desmethoxyrapamycin was replaced by 0.2 mL of an aqueous propidium iodide (PI) solution (7 mg/L). To measure the proportion of living cells, cells were permeabilized by freezing the plates. After thawing the plates, fluorescence was measured using the Cytofluor 4000 microplate reader (excitation 530 nm, emission 620 nm), giving a direct relationship to the total number of viable cells.

Growth inhibition was expressed as treated/control×100 (% T/C). For active compounds, $IC_{50}$ & $IC_{70}$ values were estimated by plotting compound concentration versus cell viability.

Monolayer Assay—Protocol 2:

The human tumor cell lines of the National Cancer Institute (NCI) cancer screening panel were grown in RPMI 1640 medium containing 5% fetal bovine serum and 2 mM L-glutamine (Boyd and Paull, 1995). Cells were inoculated into 96 well microtiter plates in 0.1 mL at plating densities ranging from 5,000 to 40,000 cells/well depending on the doubling time of individual cell lines. After cell inoculation, the microtiter plates were incubated at 37° C., 5% $CO_2$, 95% air and 100% relative humidity for 24 h prior to addition of experimental drugs.

After 24 h, two plates of each cell line were fixed in situ with trichloroacetic acid (TCA), to represent a measurement of the cell population for each cell line at the time of drug addition (Tz). Experimental drugs were solubilized in dimethyl sulfoxide at 400-fold the desired final maximum test concentration and stored frozen prior to use. At the time of drug addition, an aliquot of frozen concentrate was thawed and diluted to twice the desired final maximum test concentration with complete medium containing 0.05 mg/mL gentamicin. Additional four, 10-fold or ½ log serial dilutions were made to provide a total of five drug concentrations plus control. Aliquots of 0.1 mL of these different drug dilutions were added to the appropriate microtiter wells already containing 0.1 mL of medium, resulting in the required final drug concentrations.

Following drug addition, the plates were incubated for an additional 48 h at 37° C., 5% $CO_2$, 95% air, and 100% relative humidity. For adherent cells, the assay was terminated by the addition of cold TCA. Cells were fixed in situ by the gentle addition of 0.05 mL of cold 50% (w/v) TCA (final concentration, 10% TCA) and incubated for 60 minutes at 4° C. The supernatant was discarded, and the plates were washed five times with tap water and air dried. Sulforhodamine B (SRB) solution (0.1 mL) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 0.05 mL of 80% TCA (final concentration, 16% TCA). Using the seven absorbance measurements [time zero, (Tz), control growth, (C), and test growth in the presence of drug at the five concentration levels (Ti)], the percentage growth was calculated at each of the drug concentrations levels. Percentage growth inhibition was calculated as:

$[(Ti-Tz)/(C-Tz)] \times 100$ for concentrations where $Ti \geq Tz$ $[(Ti-Tz)/Tz] \times 100$ for concentrations where $Ti < Tz$.

Three dose response parameters were calculated for each experimental agent. Growth inhibition of 50% (GI50) was calculated from [(Ti−Tz)/(C−Tz)]×100=50, which is the drug concentration resulting in a 50% reduction in the net protein increase (as measured by SRB staining) in control cells during the drug incubation. The drug concentration resulting in total growth inhibition (TGI) was calculated from Ti=Tz. The LC50 (concentration of drug resulting in a 50% reduction in the measured protein at the end of the drug treatment as compared to that at the beginning) indicating a net loss of cells following treatment was calculated from [(Ti−Tz)/Tz]×100=−50.

Multi-drug resistant cell lines within the 60 cell line panel were identified by the NCI as high P-gp containing cell lines as identified by rhodamine B efflux (Lee et al., 1994) and by PCR detection of mRNA of mdr-1 (Alvarez et al., 1995).

Example 1

Fermentation and Isolation of 39-desmethoxyrapamycin

39-Desmethoxyrapamycin is produced by growing cultures of *S. hygroscopicus* MG2-10 [IJMNOQLhis] and feeding with cyclohexanecarboxylic acid (CHCA) as described below.

Liquid Culture

A vegetative culture of *S. hygroscopicus* MG2-10 [IJMNOQLhis] was cultivated as described in Materials & Methods. Production cultures were inoculated with vegetative culture at 0.5 mL into 7 mL medium 3 in 50 mL tubes. Cultivation was carried out for 7 days, 26° C., 300 rpm. One millilitre samples were extracted 1:1 acetonitrile with shaking for 30 min, centrifuged 10 min, 13,000 rpm and analysed and quantitated according to analysis Method B (see Materials & Methods). Confirmation of product was determined by mass spectrometry using analysis Method C (see Materials & Methods).

The observed rapamycin analogue was proposed to be the desired 39-desmethoxyrapamycin on the basis of the analytical data described under characterisation below.

Fermentation

A primary vegetative culture in Medium 4 of *S. hygroscopicus* MG2-10 [IJMNOQLhis] was cultivated essentially as described in Materials & Methods. A secondary vegetative culture in Medium 4 was inoculated at 10% v/v, 28° C., 250 rpm, for 24 h. Vegetative cultures were inoculated at 5% v/v into medium 5 (see Materials & Methods) in a 20 L fermenter. Cultivation was carried out for 6 days at 26° C., 0.5 vvm. ≧30% dissolved oxygen was maintained by altering the impeller tip speed, minimum tip speed of 1.18 ms$^{-1}$ maximum tip speed of 2.75 ms$^{-1}$. The feeding of cyclohexanecarboxylic acid was carried out at 24 and 48 hours after inoculation to give a final concentration of 2 mM.

Extraction and Purification

The fermentation broth (30 L) was stirred with an equal volume of methanol for 2 hours and then centrifuged to pellet the cells (10 min, 3500 rpm). The supernatant was stirred with Diaion® HP20 resin (43 g/L) for 1 hour and then filtered. The resin washed batchwise with acetone to strip off the rapamycin analogue and the solvent was removed in vacuo. The aqueous concentrate was then diluted to 2 L with water and extracted with EtOAc (3×2 L). The solvent was removed in vacuo to give a brown oil (20.5 g).

The extract was dissolved in acetone, dried onto silica, applied to a silica column (6×6.5 cm diameter) and eluted with a stepwise gradient of acetone/hexane (20%-40%). The rapamycin analogue-containing fractions were pooled and the solvent removed in vacuo. The residue (2.6 g) was further chromatographed (in three batches) over Sephardic LH20, eluting with 10:10:1 chloroform/heptane/ethanol. The semi-purified rapamycin analogue (1.7 g) was purified by reverse phase (C18) preparative HPLC using a Gilson HPLC, eluting a Phenomenex 21.2×250 mm Luna 5 μm C18 BDS column with 21 mL/min of 65% acetonitrile/water. The most pure fractions (identified by analytical HPLC, Method B) were combined and the solvent removed in vacuo to give 39-desmethoxyrapamycin (563 mg).

Characterisation

The $^1$H NMR spectrum of 39-desmethoxyrapamycin was equivalent to that of a standard (P. Lowden, Ph.D. Dissertation, University of Cambridge, 1997).

Figure 2:
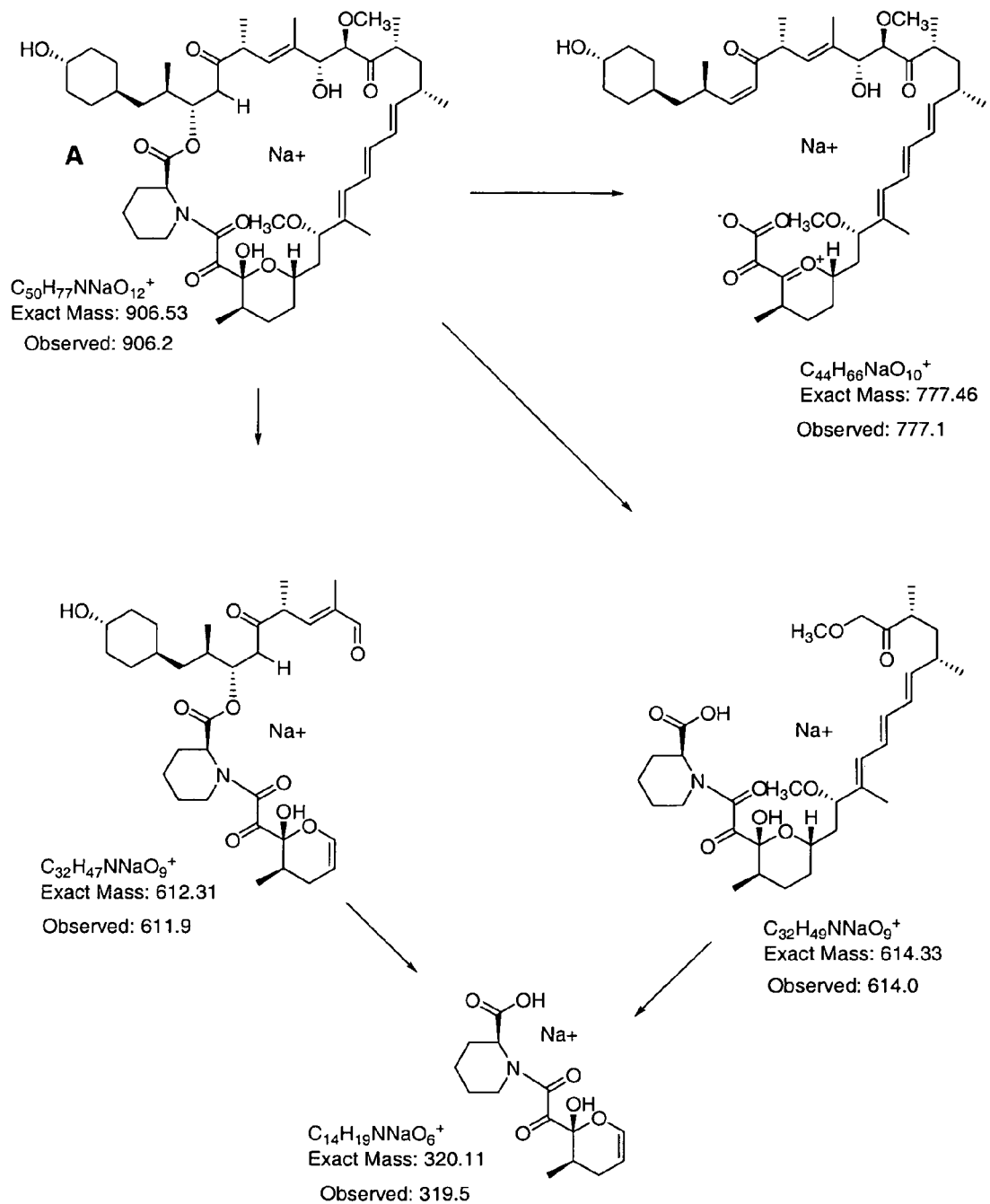
FIG. 2: shows the fragmentation pathway for 39-desmethoxyrapamycin

LCMS and LCMS$^n$ analysis of culture extracts showed that the m/z ratio for the rapamycin analogue is 30 mass units lower than that for rapamycin, consistent with the absence of a methoxy group. Ions observed: [M−H] 882.3, [M+NH$_4$]$^+$ 901.4, [M+Na]$^+$ 906.2, [M+K]$^+$ 922.2. Fragmentation of the sodium adduct gave the predicted ions for 39-desmethoxyrapamycin following a previously identified fragmentation pathway (FIG. 2) (J. A. Reather, Ph.D. Dissertation, University of Cambridge, 2000). This mass spectrometry fragmentation data narrows the region of the rapamycin analogue where the loss of a methoxy has occurred to the fragment C28-C42 that contains the cyclohexyl moiety.

These mass spectrometry fragmentation data are entirely consistent with the structure of 39-desmethoxyrapamycin Example 2

In Vitro Bioassays for Anticancer Activity

In Vitro Evaluation of Anticancer Activity of 39-desmethoxyrapamycin

In vitro evaluation of 39-desmethoxyrapamycin for anticancer activity in a panel of 12 human tumour cell lines in a monolayer proliferation assay was carried out as described as Protocol 1 in the general methods above using a modified propidium iodide assay.

The results are displayed in Table 2 below, each result represents the mean of duplicate experiments. Table 3 shows the IC$_{50}$ and IC$_{70}$ for the compounds and rapamycin across the cell lines tested.

TABLE 2

| | Test/Control (%) at drug concentration | | | |
|---|---|---|---|---|
| | Rapamycin | | 39-desmethoxyrapamycin | |
| Cell line | 1 μM | 10 μM | 1 μM | 10 μM |
| SF268 | 53.5 | 46 | 57.5 | 23 |
| 251L | 75.5 | 40 | 86 | 32.5 |
| H460 | 67 | 66 | 71 | 55.5 |
| MCF7 | 68.5 | 26.5 | 92.5 | 18.5 |
| MDA231 | 67 | 63.5 | 68 | 37.5 |
| MDA468 | 56.5 | 32 | 65 | 13.5 |
| 394NL | 45 | 44 | 48 | 40.5 |
| OVCAR3 | 69 | 69.5 | 77.5 | 62 |
| DU145 | 50.5 | 54 | 65.5 | 44.5 |
| LNCAP | 61 | 34 | 74.5 | 28.5 |
| A498 | 58.5 | 48.5 | 62.5 | 43.5 |
| 1138L | 42 | 21.5 | 52 | 9.5 |

TABLE 3

|  | Rapamycin | 39-desmethoxyrapamycin |
|---|---|---|
| Mean IC$_{50}$ (microM) | 3.5 | 3.25 |
| Mean IC$_{70}$ (microM) | 9.1 | 6.95 |

In Vitro Evaluation of Multi-drug Resistant (MDR) Selective Anticancer Activity of 39-desmethoxyrapamycin In vitro evaluation of 39-desmethoxyrapamycin for selective MDR anticancer activity in the NCI 60 cell line panel of human tumour cell lines in a monolayer proliferation assay was carried out as described in Protocol 2, Materials & Methods using an SRB based assay. The results are displayed in Table 4 below:

TABLE 4

In vitro activity against high MDR-expressing cell lines

| | Log GI$_{50}$ | | | | |
|---|---|---|---|---|---|
| Compound | NSCLC HOP-62 | Colon SW-620 | CNS SF295 | Renal A498 | Renal UO-31 |
| 39-desmethoxyrapamycin | −8.3 | −8.3 | −5.85 | −7.07 | −8.3 |
| rapamycin | −6.63 | −4.60 | −7.0 | −6.60 | −7.0 |

It can be seen that with the exception of one cell line, 39-desmethoxyrapamycin has equivalent or improved efficacy against high MDR-expressing cell lines when compared to rapamycin.

Example 3

In Vitro ADME Assays

Caco-2 Permeation Assay

Confluent Caco-2 cells (L1, A. P., 1992; Grass, G. M., et al., 1992, Volpe, D. A., et al., 2001) in a 24 well Corning Costar Transwell format were provided by In Vitro Technologies Inc. (IVT Inc., Baltimore, Md., USA). The apical chamber contained 0.15 mL Hank's balanced buffer solution (HBBS) pH 7.4, 1% DMSO, 0.1 mM Lucifer Yellow. The basal chamber contained 0.6 mL HBBS pH 7.4, 1% DMSO. Controls and tests were incubated at 37° C. in a humidified incubator, shaken at 130 rpm for 1 h. Lucifer Yellow permeates via the paracellular (between the tight junctions) route only, a high Apparent Permeability (P$_{app}$) for Lucifer Yellow indicates cellular damage during assay and all such wells were rejected. Propranolol (good passive permeation with no known transporter effects) & acebutalol (poor passive permeation attenuated by active efflux by P-glycoprotein) were used as reference compounds. Compounds were tested in a uni- and bi-directional format by applying compound to the apical or basal chamber (at 0.01 mM). Compounds in the apical or basal chambers were analysed by HPLC-MS (Method A, see Materials & Methods). Results were expressed as Apparent Permeability, P$_{app}$, (nm/s) and as the Flux Ratio (A to B versus B to A).

$$Papp\ (nm/s) = \frac{Volume\ Acceptor}{Area \times [donor]} \times \frac{\Delta[acceptor]}{\Delta time}$$

Volume Acceptor: 0.6 ml (A>B) and 0.15 ml (B>A)
Area of monolayer: 0.33 cm2
Δtime: 60 min A positive value for the Flux Ratio indicates active efflux from the apical surface of the cells.

Human Liver Microsomal (HLM) Stability Assay

Liver homogenates provide a measure of a compounds inherent vulnerability to Phase I (oxidative) enzymes, including CYP450s (e.g. CYP2C8, CYP2D6, CYP1A, CYP3A4, CYP2E1), esterases, amidases and flavin monooxygenases (FMOs).

The half life (T½) of test compounds was determined, on exposure to Human Liver Microsomes, by monitoring their disappearance over time by LC-MS. Compounds at 0.001 mM were incubated at for 40 min at 37° C., 0.1 M Tris-HCl, pH 7.4 with human microsomal sub-cellular fraction of liver at 0.25 mg/mL protein and saturating levels of NADPH as co-factor. At timed intervals, acetonitrile was added to test samples to precipitate protein and stop metabolism. Samples were centrifuged and analysed for parent compound using analytical Method A (see Materials & Methods).

TABLE 5

In vitro ADME Assay results

| | Compound | |
|---|---|---|
| Test | Rapamycin | 39-desmethoxyrapamycin |
| Caco-2: | | |
| Papp (nm/s) | 2 | 29 |
| Efflux Ratio | 458 | 15 |
| HLM stability: | | |
| T½ min | 40 | 59 |

Example 4

In Vitro Binding Assays

FKBP12

FKBP12 reversibly unfolds in the chemical denaturant guanidinium hydrochloride (GdnHCl) and the unfolding can be monitored by the change in the intrinsic fluorescence of the protein (Main et al, 1998). Ligands which specifically bind and stabilise the native state of FKBP12 shift the denaturation curve such that the protein unfolds at higher concentrations of chemical denaturant (Main et al, 1999). From the difference in stability, the ligand-binding constant can be determined using equation 1.

$$\Delta G_{app} = \Delta G_{D-N}^{H_2O} + RT\ln\left(1 + \frac{[L]}{K_d}\right) \tag{1}$$

where $\Delta G_{app}$ is the apparent difference in free energy of unfolding between free and ligand-bound forms, $\Delta G_{D-N}^{H_2O}$ is the free energy of unfolding in water of free protein, [L] the concentration of ligand and $K_d$ the dissociation constant for the protein-ligand complex (Meiering et al, 1992). The free energy of unfolding can be related to the midpoint of the unfolding transition using the following equation:

$$\Delta G_{D-N}^{H_2O} = m_{D-N}[D]_{50\%} \tag{2}$$

where $m_{D-N}$ is a constant for a given protein and given denaturant and which is proportional to the change in degree of exposure of residues on unfolding (Tanford 1968 and Tanford 1970), and $[D]_{50\%}$ is the concentration of denaturant corresponding to the midpoint of unfolding. We define $\Delta\Delta G_{D-N}^{L}$, the difference in the stability of FKBP12 with rapamycin and unknown ligand (at the same ligand concentration), as:

$$\Delta\Delta G_{D-N}^{L} = <m_{D-N}>\Delta[D]_{50\%} \quad (3)$$

where $<m_{D-N}>$ is the average m-value of the unfolding transition and $\Delta[D]_{50\%}$ the difference in midpoints for the rapamycin-FKBP12 unfolding transition and unknown-ligand-FKBP12 complex unfolding transition. Under conditions where $[L]>K_d$, then, $\Delta\Delta G_{D-N}$ can be related to the relative $K_d$s of the two compounds through equation 4:

$$\Delta\Delta G_{D-N}^{L} = RT \ln \frac{K_d^x}{K_d^{rap}} \quad (4)$$

where $K_d^{rap}$ is the dissociation constant for rapamycin and $K_d^X$ is the dissociation constant for unknown ligand X. Therefore, $$K_d^x = K_d^{rap} \exp\left(\frac{<m_{D-N}>\Delta[D]_{50\%}}{RT}\right) \quad (5)$$

For the determination of the $K_d$ of 39-desmethoxyrapamycin, the denaturation curve was fitted to generates values for $m_{D-N}$ and $[D]_{50\%}$, which were used to calculate an average m-value, $<m_{D-N}>$, and $\Delta[D]_{50\%}$, and hence $K_d^X$. The literature value of $K_d^{rap}$ of 0.2 nM is used.

Table 6—In Vitro FKBP12 Binding Assay Results

TABLE 6

In vitro FKBP12 binding assay results

|  | FKBP12 $K_d$ (nM) |
| --- | --- |
| rapamycin | 0.2 |
| 39-desmethoxyrapamycin | 0.7 | mTOR

Inhibition of mTOR can be established indirectly via the measurement of the level of phosphorylation of the surrogate markers of the mTOR pathway and p70S6 kinase and S6 (Brunn et al., 1997; Mothe-Satney et al., 2000; Tee and Proud, 2002; Huang and Houghton, 2002).

HEK293 cells were co-transfected with FLAG-tagged mTOR and myc-tagged Raptor, cultured for 24 h then serum starved overnight. Cells were stimulated with 100 nM insulin then harvested and lysed by 3 freeze/thaw cycles. Lysates were pooled and equal amounts were immunoprecipitated with FLAG antibody for the mTOR/Raptor complex. Immunoprecipitates were then processed: samples treated with compound (0.00001 to 0.003 mM) were pre-incubated for 30 min at 30° C. with FKBP12/rapamycin, FKBP12/39-desmethoxyrapamycin or vehicle (DMSO), non-treated samples were incubated in kinase buffer. Immunoprecipitates were then subject to in vitro kinase assay in the presence of 3 mM ATP, 10 mM Mn2+ and GST-4E-BP1 as substrate. Reactions were stopped with 4× sample buffer then subjected to 15% SDS-PAGE, wet transferred to PVDF membrane then probed for phospho-4E-BP1 (T37/46).

Alternatively, HEK293 cells were seeded into 6 well plates and pre-incubated for 24 h and then serum starved overnight. Cells were then pre-treated with vehicle or compound for 30 min at 30° C., then stimulated with 100 nM insulin for 30 min at 30° C. and lysed by 3 freeze/thaw cycles and assayed for protein concentration. Equal amounts of protein were loaded and separated on SDS-PAGE gels. The protein was then wet transferred to PVDF membrane and probed for phospho-S6 (S235/36) or phospho-p70 S6K (T389).

Figure 3:
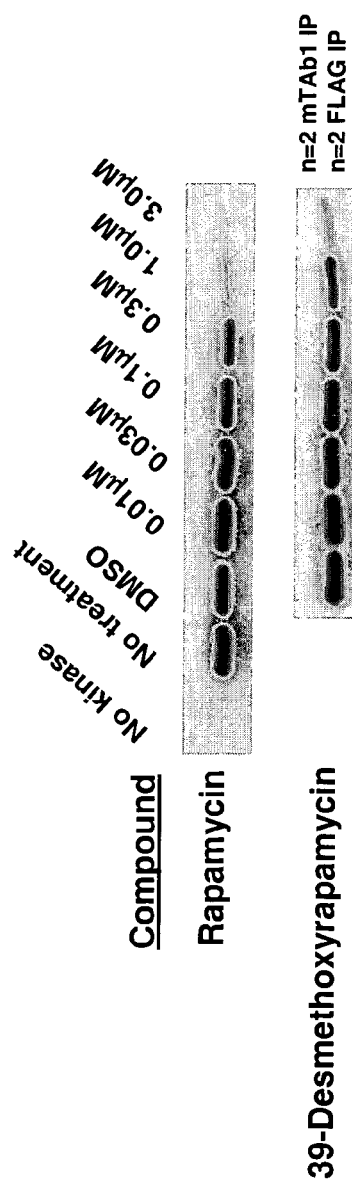
FIG. 3: shows western blots summarizing the mTOR inhibitory activity of 39-desmethoxyrapamycin and rapamycin.
Figure 3:

The results of these experiments are summarised as FIG. 3

Example 5

In Vitro P-gp Substrate Assay

Cell Lines

The cell lines used in the present study (MACL MCF7 and MACL MCF7 ADR) were both provided by the National Cancer Institute, USA.

Cells were routinely passaged once or twice weekly. They were maintained in culture for no more than 20 passages. All cells were grown at 37° C. in a humidified atmosphere (95% air, 5% $CO_2$) in RPMI 1640 medium (PAA, Cölbe, Germany) supplemented with 5% fetal calf serum (PAA, Cölbe, Germany) and 0.1% Gentamicin (PAA, Cölbe, Germany).

Assay Protocol

A modified propidium iodide assay based on protocol 1 described above was used to assess the effects of 39-desmethoxyrapamycin (Dengler et al, 1995). Briefly, cells were harvested from exponential phase cultures by trypsination, counted and plated in 96 well flat-bottomed microtiter plates at a cell density of 5.000 cells/well. After a 24 h recovery to allow the cells to resume exponential growth, 0.01 mL of Verapamil at a concentration of 0.18 mg/mL or 0.01 mL culture medium were added to the cells in order to yield a final concentration of Verapamil in the wells of 0.01 mg/mL. This concentration was found in previous experiments to be non-toxic to the cells. Culture medium containing 39-desmethoxyrapamycin, taxol or culture medium alone (for the control wells) was added at 0.01 mL per well. The compounds were applied in triplicates in 8 concentrations in half log steps ranging from 0.03 mM down to 10 nM. Following 3 days of continuous drug exposure, medium or medium with compound was replaced by 0.2 mL of an aqueous propidium iodide (PI) solution (7 mg/L). Since PI only passes leaky or lysed membranes, DNA of dead cells will be stained and measured, while living cells will not be stained. To measure the proportion of living cells, cells were permeabilized by freezing the plates, resulting in death of all cells. After thawing of the plates, fluorescence was measured using the Cytofluor 4000 microplate reader (excitation 530 nm, emission 620 nm), giving a direct relationship to the total cell number. Growth inhibition was expressed as Test/Control×100 (% T/C). Assays were only considered evaluable if the positive control (Taxol) induced a shift in tumor growth inhibition in the presence and absence of Verapamil and if vehicle treated control cells had a fluorescence intensity >500.

Preparation of 39-desmethoxyrapamycin Testing Solutions

A stock solution of 3.3 mM of 39-desmethoxyrapamycin was prepared in DMSO and stored at −20° C. The stock solution was then thawed on the day of use and stored at room temperature prior and during dosing. The dilution steps were carried out using RPMI 1640 medium and to result in solutions of 18-fold the final concentration.

Results

Figure 4:
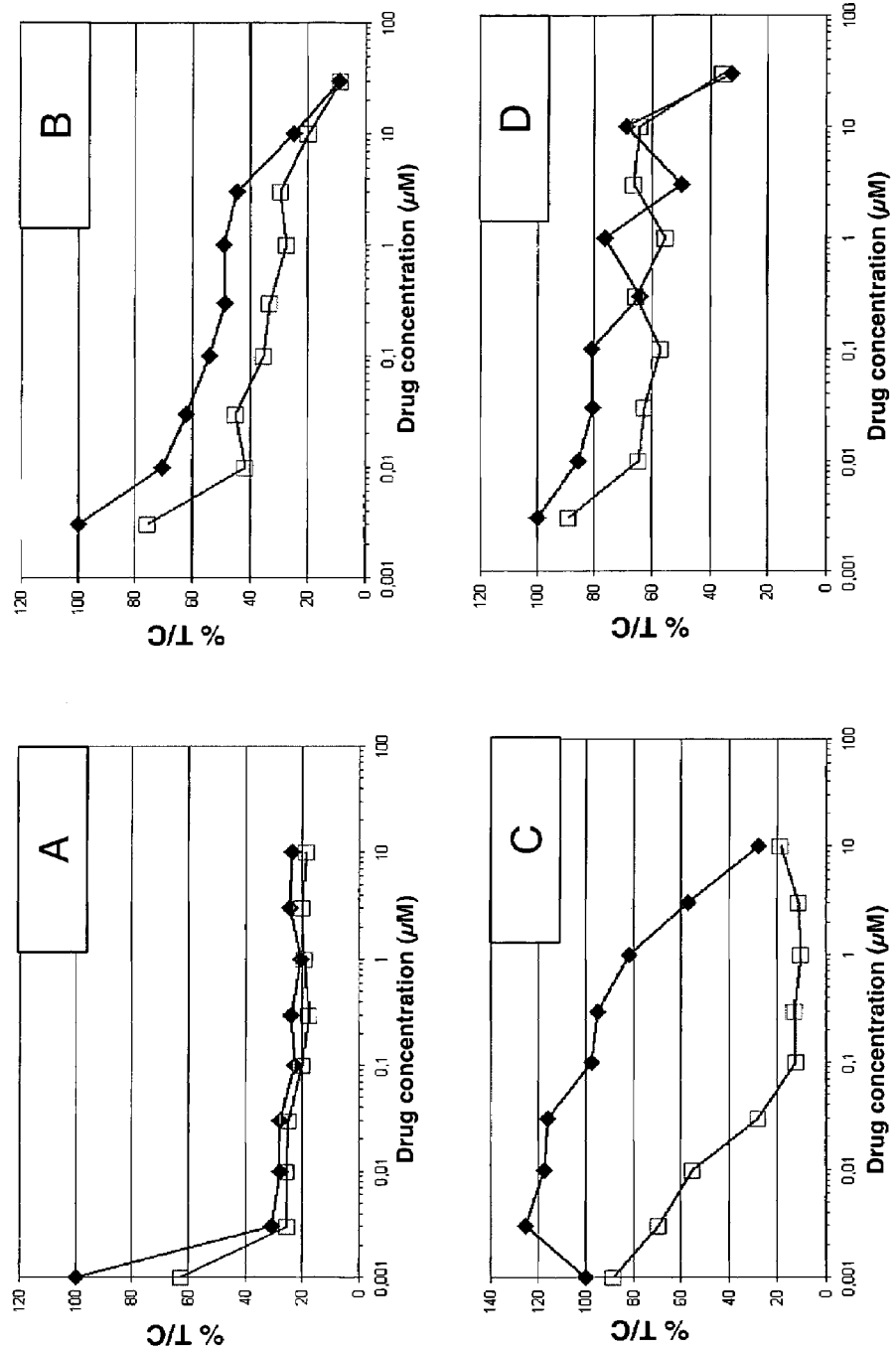
FIG. 4: the % T/C values at all test concentrations for paclitaxel (A and C) and 39-desmethoxyrapamycin (B and D) in normal (A and B) or high P-gp expressing (C and D) cell lines.

FIG. 4 shows four graphs demonstrating the % T/C values at all test concentrations for paclitaxel (A and C) and 39-desmethoxyrapamycin (B and D) in normal (A and B) or high P-gp expressing (C and D) cell lines. The filled diamonds represent the values after the administration of paclitaxel or 39-desmethoxyrapamycin alone, the open squares represent the values after the administration of paclitaxel or 39-desmethoxyrapamycin in the presence of 0.01 mg/mL Verapamil (a P-gp inhibitor).

Paclitaxel, a known P-gp substrate showed reduced potency in inhibiting P-gp expressing cancer cell line MCF7 ADR and this reduced potency was restored by the co-administration of verapamil, a P-gp inhibitor (FIGS. 4A and 4C).

39-desmethoxyrapamycin did not show a significant shift in the growth proliferation curves in the P-gp expressing cell line MCF7 ADR either with or without verapamil (FIGS. 4B and 4D) demonstrating that 39-desmethoxyrapamycin is not a substrate for P-gp.

REFERENCES

Alvarez, M., Paull, K., Monks, A., Hose, C., Lee, J. S., Weinstein, J., Grever, M., Bates, S., Fojo, T., (1995). "Generation of a drug resistance profile by quantitation of mdr-1/P-glycoprotein in the cell lines of the National Cancer Institute Anticancer Drug Screen", *Journal of Clinical Investigation*, 95, 2205-2214.

Baker, H., Sidorowicz, A., Sehgal, S. N., and Vézina, C. (1978) "Rapamycin (AY-22,989), a new antifungal antibiotic. III. In vitro and in vivo evaluation". *Journal of Antibiotics* 31, 539-545.

Boyd, M. R. and Paull, K. D., (1995). "Some Practical Considerations and Applications of the National Cancer Institute In Vitro Anticancer Drug Discovery Screen", *Drug Development Research* 34, 91-109, Brunn, G. J., Fadden, P., Haystead, T. A., Lawrence, J. C. Jr. (1997) "The mammalian target of rapamycin phosphorylates sites having a (Ser/Thr)-Pro motif and is activated by antibodies to a region near its COOH terminus", *J Biol. Chem.* 272(51), 32547-32550.

Brunn, G. J., Williams, J., Sabers, C., Wiederrecht, G., Lawrence, J. C., and Abraham, R. T. (1996) "Direct inhibition of the signaling functions of the mammalian target of rapamycin by the phosphoinositide 3-kinase inhibitors, wortmannin and LY294002". *EMBO Journal* 15: 5256-5267.

Crowe, A., Bruelisauer, A., Duerr, L., Guntz, P., Lemaire, M., (1999), "Absorption and intestinal metabolism of SDZ-RAD and rapamycin in rats". *Drug Metab Dispos.;* 27(5), 627-32.

Cummins, C. L., Jacobsen, W., Christians, U., Benet, L. Z., (2004) "CYP3A4-Transfected Caco-2 Cells as a Tool for Understanding Biochemical Absorption Barriers: Studies with Sirolimus and Midazolam", *The Journal of Pharmacology*, 308(1), 143-155

Dancey, J. E., (2002), "Clinical development of mammalian target of rapamycin inhibitors" *Hematol Oncol Clin N Am,* 16, 1101-1114.

Dengler W. A., Schulte J., Berger D. P., Mertelsmann R. and Fiebig H H. (1995) "Development of a propidium iodide fluorescence assay for proliferation and cytotoxicity assay". *Anti-Cancer Drugs,* 6, 522-532.

Dumont, F. J. and Q. X. Su (1995). "Mechanism of action of the immunosuppressant rapamycin". *Life Sciences* 58(5): 373-395.

Fiebig H. H., Dengler W. A. and Roth T. (1999) "Human tumor xenografts: Predictivity, characterization, and discovery of new anticancer agents". In: Fiebig H H, Burger A M (eds). Relevance of Tumor Models for Anticancer Drug Development. *Contrib. Oncol.,* 54: 29-50.

Findlay J. A, and Radics, L. (1980) *Canadian Journal of Chemistry* 58:579.

Gallant-Haidner H L, Trepanier D J, Freitag D G, Yatscoff R W. 2000, "Pharmacokinetics and metabolism of sirolimus". *Ther Drug Monit.* 22(1), 31-5.

Grass, G. M., Rubas, W., Jezyk, N., (1992) "Evaluation of CACO-2 monolayers as a predictor of drug permeability in colonic tissues". *FASEB Journal,* 6, A1002.

Gregory M A, Gaisser S, Lill R E, Hong H, Sheridan R M, Wilkinson B, Petkovic H, Weston A J, Carletti I, Lee H L, Staunton J, Leadlay P F. (2004) "Isolation and characterization of pre-rapamycin, the first macrocyclic intermediate in the biosynthesis of the immunosuppressant rapamycin by *S. hygroscopicus*". *Angew Chem Int Ed Engl.* 43(19), 2551-3

Huang, S. and Houghton, P. J., 2002. "Mechanisms of resistance to rapamycins". *Drug Resist. Update,* 4(6), 378-391.

Huang, S., M. A. Bjornsti, and Houghton P J. (2003). "Rapamycins: mechanism of action and cellular resistance." *Cancer Biol Ther* 2(3): 222-32.

Kahan, B. D., Chang, J. Y., and Sehgal, S. N. (1991) "Preclinical evaluation of a new potent immunosuppressive agent, rapamycin". *Transplantation* 52: 185-191.

Kirchner, G. I., Winkler, M., Mueller L., Vidal, C., Jacobsen, W., Franzke, A., Wagner, S., Blick, S., Manns M. P., and Sewing K.-F. (2000) "Pharmacokinetics of SDZ RAD and cyclosporin including their metabolites in seven kidney graft patients after the first dose of SDZ RAD". British Journal of Clinical Pharmacology 50:449-454.

Kuhn B, Jacobsen W, Christians U, Benet L Z, Kollman P A. (2001), "Metabolism of sirolimus and its derivative everolimus by cytochrome P450 3A4: insights from docking, molecular dynamics, and quantum chemical calculations". *J Med. Chem.* 44(12), 2027-34.

Kuo, C. J., Chung, J. K., Fiorentino, D. F., Flanagan, W. M., Blenis, J., and Crabtree, G. R. (1992) "Rapamycin selectively inhibits interleukin-2 activation of p70 S6 kinase". *Nature* 358: 70-73.

Lampen A, Zhang Y, Hackbarth I, Benet L Z, Sewing K F, Christians U. (1998) "Metabolism and transport of the macrolide immunosuppressant sirolimus in the small intestine". *J Pharmacol Exp Ther.* 285(3), 1104-12.

Langmann T, Mauerer R, Zahn A, Moehle C, Probst M, Stremmel W, Schmitz G. (2003) "Real-time reverse transcription-PCR expression profiling of the complete human ATP-binding cassette transporter superfamily in various tissues". *Clin Chem.* 49(2), 230-8.

Laplante A, Demeule M, Murphy G F, Beliveau R. (2002) "Interaction of immunosuppressive agents rapamycin and its analogue SDZ-RAD with endothelial P-gp". *Transplant Proc.* 34(8), 3393-5.

Lee, J-S, Paull, K., Alvarez, M., Hose, C., Monks, A., Grever, M., Fojo, A. T., Bates, S. E., 1994. "Rhodamine efflux patterns predict P-glycoprotein substrates in the National Cancer Institute drug screen". *Molecular Pharmacology* 46, 627-638.

Lee J K, Bussey K J, Gwadry F G, Reinhold W, Riddick G, Pelletier S L, Nishizuka S, Szakacs G, Annereau J P, Shankavaram U, Lababidi S, Smith L H, Gottesman M M, Weinstein J N. (2003) "Comparing cDNA and oligonucleotide array data: concordance of gene expression across platforms for the NCI-60 cancer cells". *Genome Biol.* 4(12), R82.

Li, A. P. (1992) "Screening for human ADME/Tox drug properties in drug discovery". *Drug Discovery Today,* 6, 357-366.

Lowden, P. A. S., (1997) Ph.D. Dissertation, University of Cambridge. "Studies on the biosynthesis of rapamycin".

Main, E. R. G., Fulton, K. F. & Jackson, S. E. (1998). "The Context-Dependent Nature of Destabilising Mutations on the Stability of FKBP12". *Biochemistry* 37, 6145-6153.

Main, E. R. G., Fulton, K. F. & Jackson, S. E. (1999). "Folding of FKBP12: Pathway of Folding and Characterisation of the Transition State". *J. Mol. Biol.* 291, 429-444.

McAlpine, J. B., Swanson S. J., Jackson, M., Whittern, D. N. (1991). "Revised NMR assignments for rapamycin". *Journal of Antibiotics* 44: 688-690.

Meiering, E. M., Serrano, L. & Fersht, A. R. (1992). "Effect of Active Site Residues in Barnase on Activity and Stability". *J. Mol. Biol.* 225, 585-589.

Mothe-Satney, I., Brunn, G. J., McMahon, L. P., Capaldo, C. T., Abraham, R. T., Lawrence, J. C. Jr-. (2000) "Mammalian target of rapamycin-dependent phosphorylation of PHAS-I in four (S/T)P sites detected by phospho-specific antibodies". *J Biol. Chem.* 275(43), 33836-33843.

Paiva, N. L., Demain, A. L., and Roberts, M. F. (1991) "Incorporation of acetate, propionate, and methionine into rapamycin By *Streptomyces hygroscopicus*" *Journal of Natural Products* 54: 167-177.

Perin, E C, (2005), "Choosing a Drug-Eluting Stent: A Comparison Between CYPHER and TAXUS", *Reviews in Cardiovascular Medicine,* 6 (suppl 1), pp S13-S21.

Persidis A. (1999), "Cancer multidrug resistance" Nat. Biotechnol. 17: 94-5

Reather, J. A., (2000), Ph.D. Dissertation, University of Cambridge. "Late steps in the biosynthesis of macrocyclic lactones".

Roth T., Burger A. M., Dengler W., Willmann H. and Fiebig H. H. (1999) "Human tumor cell lines demonstrating the characteristics of patient tumors as useful models for anticancer drug screening". In: Fiebig H H, Burger A M (eds). Relevance of Tumor Models for Anticancer Drug Development. *Contrib. Oncol.,* 54: 145-156.

Sedrani, R., Cottens, S., Kallen, J., and Schuler, W. (1998) "Chemical modifications of rapamycin: the discovery of SDZ RAD". *Transplantation Proceedings* 30: 2192-2194.

Sehgal, S. N., Baker, H., and Vézina, C. (1975) "Rapamycin (AY-22,989), a new antifungal antibiotic II. Fermentation, isolation and characterization". *The Journal of Antibiotics* 28: 727-733.

Stein U, Jurchott K, Schlafke M, Hohenberger P. (2002) "Expression of multidrug resistance genes MVP, MDR1, and MRP1 determined sequentially before, during, and after hyperthermic isolated limb perfusion of soft tissue sarcoma and melanoma patients". J Clin Oncol. 20(15): 3282-92.

Szakacs G, Annereau J P, Lababidi S, Shankavaram U, Arciello A, Bussey K J, Reinhold W, Guo Y, Kruh G D, Reimers M, Weinstein J N, Gottesman M M. 2004, "Predicting drug sensitivity and resistance: profiling ABC transporter genes in cancer cells". Cancer Cell. 6(2): 129-37.

Tanford, C. (1968). "Protein Denaturation". *Adv. Prot. Chem.* 23, 121-282.

Tanford, C. (1970). "Protein Denaturation. Part C. Theoretical models for the mechanism of denaturation". *Advances in Protein Chemistry* 24, 1-95

Tee, A. R. and Proud, C. G. (2002) "Caspase cleavage of initiation factor 4E-binding protein 1 yields a dominant inhibitor of Cap-dependent translation and reveals a novel regulatory motif". *Mol. Cell. Biol.* 22, 1674-1683

Trepanier D J, Gallant H, Legatt D F, Yatscoff R W. (1998), "Rapamycin: distribution, pharmacokinetics and therapeutic range investigations: an update". *Clin Biochem.* 31(5): 345-51.

Vézina, C., Kudelski, A., and Sehgal, S. N. (1975) "Rapamycin (AY-22,989), a new antifungal antibiotic. I. Taxonomy of the producing streptomycete and isolation of the active principle". *The Journal of Antibiotics* 28: 721-726.

Volpe, D. A., Faustino, P. J., Yu, L. X., (2001) "Towards standardisation of an in vitro method of drug absorption". *Pharmacopeial Forum,* 27, 2916-2922.

Yu, K., Toral-Barza, L., Discafani, C., Zhang, W. G., Skotnicki, J., Frost, P., Gibbons, J. J. (2001) "mTOR, a novel target in breast cancer: the effect of CCI-779, an mTOR inhibitor, in preclinical models of breast cancer". *Endocrine-Related Cancer* 8:249-258.

The invention claimed is:

1. A method of treating multiple sclerosis in a patient in need thereof, comprising the administration of an effective amount of a medicament comprising 39-desmethoxyrapamycin or a pharmaceutically acceptable salt thereof, to said patient.

2. The method of claim 1, wherein said 39-desmethoxyrapamycin or a pharmaceutically acceptable salt thereof is orally administered.

3. The method of claim 1, wherein said 39-desmethoxyrapamycin or a pharmaceutically acceptable salt thereof is administered via a drug-eluting stent.

4. The method of claim 1 further comprising the administration of at least one immunoregulatory agent.

5. The method of claim 4, wherein said immunoregulatory agent is selected from the group consisting of azathioprine, corticosteroids, cyclophosphamide, cyclosporin A, FK506, Mycophenolate Mofetil, OKT-3 and ATG.

* * * * *